US00PP21110P2

(12) United States Plant Patent
Kitamura

(10) Patent No.: US PP21,110 P2
(45) Date of Patent: Jun. 29, 2010

(54) ***PHLOX* PLANT NAMED 'SUNPHLOSUPAPI'**

(50) Latin Name: *Phlox drummondii*
Varietal Denomination: Sunphlosupapi

(75) Inventor: Kenichi Kitamura, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/383,284

(22) Filed: Mar. 23, 2009

(51) Int. Cl.
*A01H 5/00* (2006.01)

(52) U.S. Cl. ..... Plt./320
(58) Field of Classification Search ..... Plt./320
See application file for complete search history.

*Primary Examiner*—Susan B McCormick Ewoldt
(74) *Attorney, Agent, or Firm*—C. A. Whealy

(57) ABSTRACT

A new and distinct cultivar of *Phlox* plant named 'Sunphlosupapi', characterized by its upright and outwardly spreading plant habit; vigorous growth habit; freely branching and flowering habit; long flowering period; light pink-colored flowers with red purple-colored centers; and good garden performance.

1 Drawing Sheet

Botanical designation: *Phlox drummondii.*
Cultivar denomination: 'SUNPHLOSUPAPI'.

BACKGROUND OF THE INVENTION

The present invention relates to a new and distinct cultivar of *Phlox* plant, botanically known as *Phlox drummondii* and hereinafter referred to by the name 'Sunphlosupapi'.

The new *Phlox* plant is a naturally-occurring branch mutation of a proprietary selection of *Phlox drummondii* identified as code number 0Ph-18a-M, not patented. The new *Phlox* was discovered and selected by the Inventor from within a population of plants of the parent selection in a controlled greenhouse environment in Higashiomi, Shiga, Japan in August, 2006.

Asexual reproduction of the new *Phlox* plant by cuttings in a controlled greenhouse environment in Higashiomi, Shiga, Japan since September, 2006, has shown that the unique features of this new *Phlox* plant are stable and reproduced true to type in successive generations.

SUMMARY OF THE INVENTION

Plants of the new *Phlox* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunphlosupapi'. These characteristics in combination distinguish 'Sunphlosupapi' as a new and distinct cultivar of *Phlox:*

1. Upright and outwardly spreading plant habit.
2. Vigorous growth habit.
3. Freely branching and flowering habit.
4. Long flowering period.
5. Light pink-colored flowers with red purple-colored centers.
6. Good garden performance.

Plants of the new *Phlox* differ from plants of the parent selection primarily in flower color as plants of the parent selection have white-colored flowers with red purple-colored central star.

Plants of the new *Phlox* can also be compared to plants of *Phlox drummondii* 'Sunphlopin', disclosed in U.S. Plant Pat. No. 16,361. In side-by-side comparisons conducted in Higashiomi, Shiga, Japan, plants of the new *Phlox* and 'Sunphlopin' differed in the following characteristics:

1. Plants of the new *Phlox* had thicker stems than plants of 'Sunphlopin'.
2. Plants of the new *Phlox* had shorter internodes than plants of 'Sunphlopin'.
3. Plants of the new *Phlox* had smaller leaves than plants of 'Sunphlopin'.
4. Plants of the new *Phlox* and 'Sunphlopin' differed in flower color.

BRIEF DESCRIPTION OF THE PHOTOGRAPHS

The accompanying colored photographs illustrate the overall appearance of the new *Phlox*, showing the colors as true as it is reasonably possible to obtain in colored reproductions of this type. Colors in the photographs may differ slightly from the color values cited in the detailed botanical description which accurately describe the colors of the new *Phlox.*

The photograph at the top of the sheet comprises a side perspective view of a typical flowering plant of 'Sunphlosupapi' grown in a container.

The photograph at the bottom of the sheet is a close-up view of typical flowers of 'Sunphlosupapi'.

DETAILED BOTANICAL DESCRIPTION

The aforementioned photographs and following observations, measurements and values describe plants grown in Higashiomi, Shiga, Japan, under commercial practice during the late summer in an outdoor nursery with day temperatures averaging 23° C. and night temperatures averaging 13° C. Plants had been growing for seven months when the photographs and description were taken. In the following description, color references are made to The Royal Horticultural Society Colour Chart, 2001 Edition, except where general terms of ordinary dictionary significance are used.

Botanical classification: *Phlox drummondii* 'Sunphlosupapi'.

Parentage: Naturally-occurring branch mutation of a proprietary selection of *Phlox drummondii* identified as code number 0Ph-18a-M, not patented.

Propagation:

*Type.*—By cuttings.

*Time to initiate roots.*—About two to three weeks at 20° C. to 25° C.

*Time to produce a rooted young plant.*—About one to two months at 20° C. to 25° C.

*Root description.*—Fibrous; white in color.

*Rooting habit.*—Freely branching; moderately dense.

Plant description:

*Plant form/habit.*—Upright and outwardly spreading plant habit, mounding form; vigorous growth habit; freely branching habit with lateral branches potentially developing at every node; pinching enhances branching.

*Plant height.*—About 25.6 cm.

*Plant width* (*spread*).—About 39.8 cm.

*Lateral branches.*—Length: About 25.8 cm. Diameter: About 2.5 mm. Internode length: About 8 mm. Strength: Strong. Texture: Pubescent. Color: Close to 144B.

Foliage description:

*Arrangement.*—Alternate, simple; sessile.

*Length.*—About 2.2 cm.

*Width.*—About 8 mm.

*Shape.*—Lanceolate.

*Apex.*—Acute.

*Base.*—Truncate to cordate.

*Margin.*—Entire.

*Texture, upper and lower surfaces.*—Pubescent.

*Venation pattern.*—Pinnate, reticulate.

*Color.*—Developing and fully expanded leaves, upper surface: Close to 137B; venation, close to 145C. Developing and fully expanded leaves, lower surface: Close to 147B; venation, close to 145C.

Flower description:

*Flower type/habit.*—Single rotate flowers arranged in terminal and axillary cymes; flowers face mostly upright. Cymes roughly hemispherical in shape. Freely flowering habit with about three open flowers per inflorescence.

*Fragrance.*—None detected.

*Natural flowering season.*—Continuously flowering from spring to autumn in Japan.

*Postproduction longevity.*—Flowers last about five days on the plant; flowers not persistent.

*Flower buds.*—Height: About 1.45 cm. Diameter: About 3.5 mm. Shape: Clavate. Color: Close to 155A.

*Inflorescence height.*—About 4.2 cm.

*Inflorescence diameter.*—About 5.4 cm.

*Flower diameter.*—About 2.6 cm.

*Flower depth.*—About 5.8 cm.

*Tube length.*—About 1.2 cm.

*Tube diameter, base.*—About 2.3 mm.

*Petals.*—Quantity per flower: Typically five in a single whorl; petals fused at the base into a narrow tube. Length: About 1.33 cm. Lobe width: About 1.34 cm. Shape: Broadly rhombic. Apex: Obtuse. Margin: Entire. Texture, upper and lower surfaces and throat: Smooth, glabrous. Texture, tube: Pubescent. Color: Developing and fully expanded petals, upper surface: Close to 69D overlain with streaks of 83B; towards the center, between 61A and 59A. Developing and fully expanded petals, lower surface: Close to 69D. Throat: Close to 186D. Tube: Close to 146D.

*Sepals.*—Quantity per flower: Typically five in a single whorl, fused towards the base; calyx star-shaped. Length: About 3.3 mm. Width: About 1.4 mm. Shape: Lanceolate. Apex: Acute. Margin: Entire. Texture, upper and lower surfaces: Smooth, glabrous. Color, developing and fully expanded sepals, upper surface: Close to 137C. Color, developing and fully expanded sepals, lower surface: Close to 137C.

*Peduncles.*—Length: About 2 mm to 10 mm. Diameter: About 1 mm. Strength: Strong. Texture: Pubescent. Color: Close to 145B.

*Pedicels.*—Length: About 7.5 mm. Diameter: About 0.9 mm. Strength: Strong. Texture: Pubescent. Color: Close to 145B.

*Reproductive organs.*—Stamens: Quantity per flower: Typically five. Stamen length: About 3.5 mm to 7.3 mm. Anther shape: Lanceolate. Anther size: About 1.6 mm by 0.5 mm. Anther color: Close to 12A. Pollen amount: Moderate. Pollen color: Close to 15B. Pistils: Quantity per flower: One. Pistil length: About 5.1 mm. Stigma shape: Three-parted. Stigma color: Close to 1C. Style color: Close to 145C. Ovary color: Close to 143C.

*Seed/fruit.*—Seed and fruit development have not been observed.

Disease/pest resistance: Plants of the *Phlox* have not been observed to be resistant to pathogens and pests common to *Phlox*.

Garden performance: Plants of the new *Phlox* have been observed to have good garden performance and tolerate rain, wind and temperatures ranging from about 0° C. to about 35° C.

It is claimed:

1. A new and distinct *Phlox* plant named 'Sunphlosupapi' as illustrated and described.

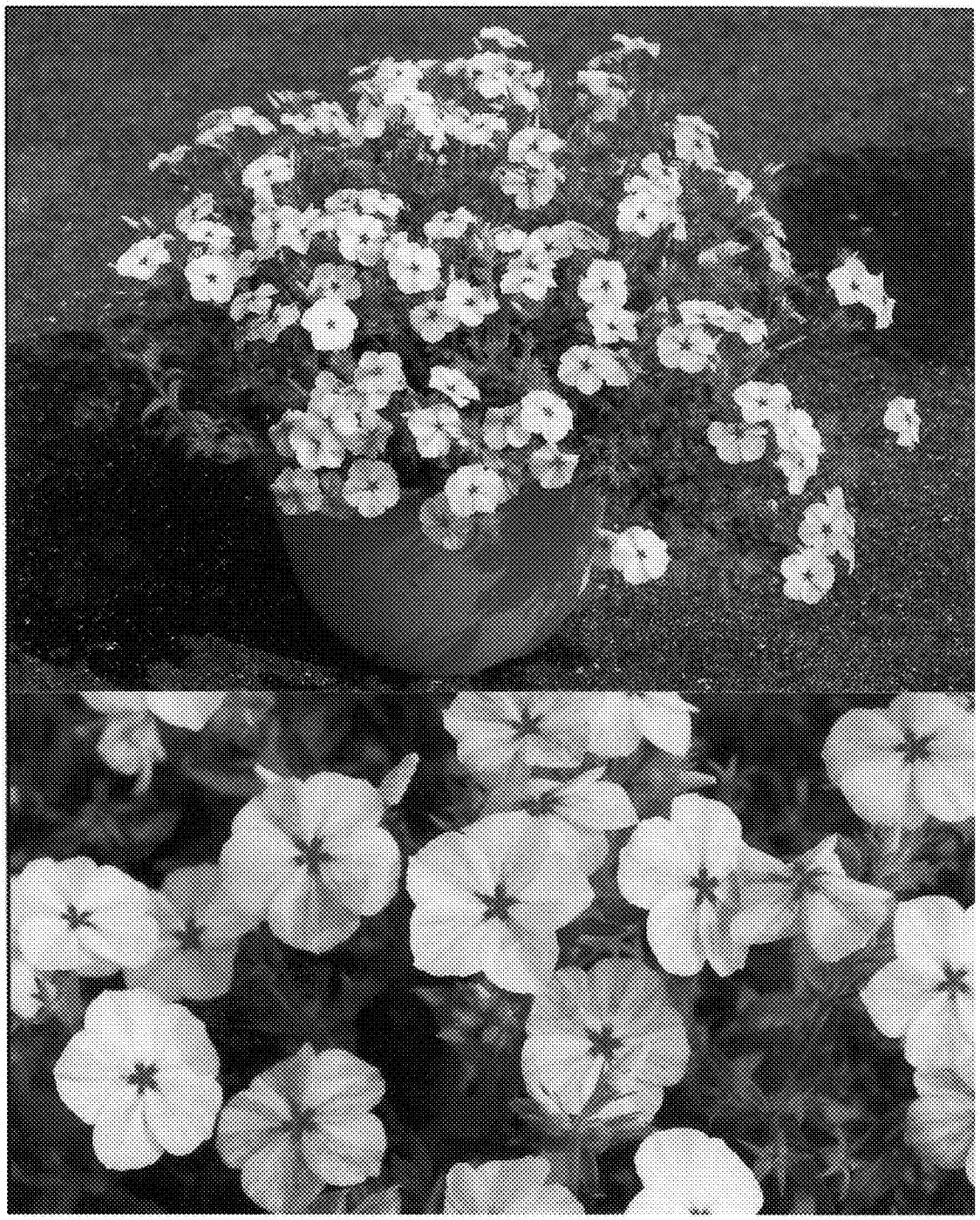

* * * * *